United States Patent [19]
Albers et al.

[11] Patent Number: 5,602,309
[45] Date of Patent: Feb. 11, 1997

[54] TRANSGENIC MICE WHICH OVEREXPRESS NERVE GROWTH FACTOR

[75] Inventors: Kathryn M. Albers; Brian M. Davis, both of Lexington, Ky.

[73] Assignee: University of Kentucky Research Foundation, Lexington, Ky.

[21] Appl. No.: 438,122

[22] Filed: May 8, 1995

Related U.S. Application Data

[63] Continuation of Ser. No. 131,424, Oct. 4, 1993, abandoned.
[51] Int. Cl.$^6$ .......................... C12N 15/00; C12P 21/00; A01K 67/00
[52] U.S. Cl. .................... 800/2; 435/172.3; 800/DIG. 1; 800/DIG. 4
[58] Field of Search ................... 800/2, DIG. 1, 800/DIG. 4; 435/172.3, 69.1, 69.5, 69.4; 424/9

[56] References Cited

U.S. PATENT DOCUMENTS

| | | | |
|---|---|---|---|
| 4,185,095 | 1/1980 | Young | 514/21 |
| 4,736,866 | 4/1988 | Leder et al. | 800/2 |
| 5,082,774 | 1/1992 | Heinrich | 435/69.1 |
| 5,175,383 | 12/1992 | Leder et al. | 800/2 |
| 5,175,384 | 12/1992 | Krimpenfort et al. | 800/2 |
| 5,175,385 | 12/1992 | Wagner et al. | 800/2 |
| 5,180,820 | 1/1993 | Barde et al. | 536/23.51 |
| 5,231,001 | 7/1993 | Kaplan et al. | 435/721 |

FOREIGN PATENT DOCUMENTS

WO93/00909  1/1993  WIPO .

OTHER PUBLICATIONS

Vassar, Robert, et al. "Tissue–specific and differentiation–specific expression of human K14 keratin gene in transgenic mice", *Proc. Natl. Acad. Sci. USA*, vol. 86, (Mar. 1989) pp. 1563–1567.

Edwards, Robert H., et al. "Directed Expression of NGF to Pancreatic β Cells in Transgenic Mice Leads to Selective Hyperinnervation of the Islets", *Cell*, vol. 58, (Jul. 14, 1989) pp. 161–170.

Patil, Nila, et al. "Specific Neuronal Expression of Human NGF Receptors in the Basal Forebrain and Cerebellum of Transgenic Mice", *Neuron*, vol. 2, (Mar. 1990) pp. 437–447.

Vassar, Robert et al. "Transgenic Mice Provide New Insights into the Role of TGF–α During Epidermal Development and Differentiation", *Genes & Development*, vol. 5, (1991) pp. 714–727.

Borrelli, Emiliana, et al. "Pituitary Hyperplasia Induced by Ectopic Expression of Nerve Growth Factor", *Proc. Natl. Acad. Sci. USA*, vol. 89, (Apr. 1992) pp. 2764–2768.

Ard, M. D., Morest, D. K. (1984). *Intl. J. Dev. Neurosci.* 2, 535–547.

Oppenheim, R. W. (1991). *Ann. Rev. Neurosci.* 14, 453–501.

Thoenen, H. and Barde, Y. A. (1980). *Physiol. Rev.* 60, 1284–1334.

Oppenheim, R. W. (1989). *Trends in Neurosci.* 12, 252–255.

Davies, A. M., Larmet, Y., Wright, E., Vogel, K. S. (1991). *J. Cell Sci.* 15, 111–116.

Oppenheim, R. W. (1981). *Studies in Developmental Biology* (ed. W. M. Cowan) pp. 74–133. Oxford University Press.

Cowan, W. M. Fawcett, J. W., O'Leary, D. D. M., and Stanfield, B. B. (1984). *Science* 225, 1258–1265.

Levi–Montalcini, R. and Booker B. (1960). *Proc. Natl. Acad. Sci. U.S.A* 46, 384–391.

(List continued on next page.)

*Primary Examiner*—Brian R. Stanton
*Attorney, Agent, or Firm*—Lowe, Price, LeBlanc & Becker

[57] ABSTRACT

Transgenic mice that express increased levels of nerve growth factor (NGF) in the epidermis and other stratified, keratinized epithelium. The nerve growth factor expressing transgenic mice are useful in the study of neurodegenerative disorders of the brain such as Parkinson's syndrome and Alzheimer's disease and for testing for drug candidates for the treatment of these diseases.

5 Claims, 8 Drawing Sheets

OTHER PUBLICATIONS

Hefti, F. (1986) *J. Neurosci.* 6, 2155–2161.

Williams, L. R., Varon, S., Peterson, G., Wictorin, K., Fischer, W., Bjorklund, A. & Gage, F. H. (1986). *Proc. Natl. Acad. Sci. U.S.A.* 83, 9231–9235.

Johnson, E. M., Gorin, P. D., Brandeis, L. D., Pearson, J. (1980). *Science* 210, 916–918.

Barde, Y. A., Edgar, D., Thoenen H. (1980). *Proc. Natl. Acad. Sci. U.S.A.* 77, (1980) 1199–1203.

Hamburger, V. and Yip, H. W. (1984). *J. Neurosci.* 4, 767–774.

Davies, A. M., Bandtlow, D., Heumann, R., Korsching, S., Rohrer, H., and Thoenen, H. (1987) *Nature* 326, 353–358).

Rohrer, H., Heumann, R., Thoenen, H. (1988). *Dev. Biol.* 128, 240–244.

Harper, S. J., and Davies, A. M. (1990). *Development* 110, 515–519.

Schweizer, J., and Winter, H. (1982) *Differentiation* 22, 19–24.

Kopan, R. and Fuchs, E. (1989) *Genes and Devel.* 3, 1–15.

Edwards et al. 1989 Cell 58: 161–170.

Davies et al. 1987. Nature 326: 353–358.

Vassar et al. 1989. Proc. Nat'l Acad. Sci., USA 86: 1563–1567.

Sandgren et al. 1990. Cell 61: 1121–1135.

Soppet et al. 1991. Cell 65: 895–903.

Khillan et al. 1986. Proc. Nat'l. Acad. Sci, USA. 83: 725–729.

TRANSGENIC MICE WHICH OVEREXPRESS NERVE GROWTH FACTOR

This application is a continuation of application Ser. No. 08/131,424 filed Oct. 4, 1993, now abandoned.

TECHNICAL FIELD

The present invention relates to transgenic mice that express increased levels of nerve growth factor (NGF) in the epidermis and other stratified, keratinized epithelium. The nerve growth factor expressing transgenic mice of the present invention are valuable to researchers that study the role of nerve growth factor and other neurotrophic factors in the development and function of the nervous system, and in the study of neurodegenerative disorders of the brain such as Parkinson's syndrome and Alzheimer's disease.

BACKGROUND

The survival of developing vertebrate neurons is thought to be dependent on access to a limited supply of target-derived neurotrophic factors. Nerve growth factor (NGF) is the most extensively characterized of these factors and has been shown to regulate the survival of discrete populations of neurons.

U.S. Pat. No. 4,185,095 to Young discloses the isolation of a nerve growth factor from mouse submandibular or salivary gland.

U.S. Pat. No. 5,082,774 to Heinrich discloses a recombinant human nerve growth factor. The nerve growth factor is in an expression vector with an adenovirus strong, major, late promoter. Heinrich discloses that the expression vector may be used to stably transfect mammalian cells such as CHO or COS cells.

U.S. Pat. No. 5,180,820 to Barde et al. discloses that NGF has been molecularly cloned.

Various transgenic mice have been patented. U.S. Pat. No. 4,736,866 to Leder et al. discloses a transgenic non-human eukaryotic animal whose germ cells and somatic cells contain an activated oncogene sequence introduced into the animal or an ancestor of the animal at an embryonic stage. The embryo of the mice were microinjected with approximately 500 copies of the RSVS-107 c-myc plasmid. The injected eggs were transferred to pseudopregnant foster families and allowed to develop to term. The plasmid contains a Rous Sarcoma Virus enhancer and promoter sequence. The resultant mice showed expression of the c-myc gene in the salivary gland, spleen, testes, lung, brain, and preputial gland and intestinal tissue.

U.S. Pat. No. 5,175,383 to Leder et al. discloses a male transgenic mouse containing germ cells and somatic cells which contain a recombinant gene which is a vertebrate gene in the Int-2/FGF family which is capable of promoting benign prostatic hyperplasia or hypertrophy. The fusion gene which is injected into the mouse embryonic tissue comprises a promoter sequence controlling transcription of the recombinant gene such as a promoter derived from the mouse mammary tumor virus and cytomegalovirus. The recombinant gene is preferably substantially homologous with (i.e., greater than 50% homologous in terms of encoded amino acid sequence) a naturally occurring, vertebrate gene in the Int-2/FGF gene family of murine growth factor encoding genes or their vertebrate counterparts, including the murine acidic or basic fibroblast growth factor genes, the murine FGF-5 gene, the murine epidermal growth factor gene, the murine insulin-like growth factor-1 and -2 gene, the murine α-transforming growth factor gene with a murine hst/KS3 gene. The transgenic mice of Leder et al. exhibit prostate hyperplasia and give sterile offspring.

U.S. Pat. No. 5,175,384 to Krimpenfort et al. discloses transgenic mice having a phenotype characterized by the substantial absence of mature T-lymphocytes. The mouse is produced by introducing a transgene into a zygote of a mouse which comprises gene fragment which encodes a T-cell antigen receptor polypeptide variant which is incapable of mediating T-cell maturation in the transgenic mouse.

U.S. Pat. No. 5,175,385 to Wagner et al. discloses the production of a transgenic mouse with enhanced viral resistance which is transmissible to its offspring. The transgenic mouse is prepared by introduction of a gene encoding a human interferon having anti-viral activity into a host mouse. The plasmid of Wagner et al. contains a methallothionein-1 promoter and the genomic human beta interferon gene. When these mice were injected with pseudorabies virus they showed an increased resistance to the virus and although many mice died they died considerably later than did the control animals.

Vassar et al., in the *Proceedings of the National Academy of Sciences*, Volume 86, pages 1563–1567, March 1989, disclose "Tissue-specific and Differentiation-specific Expression of a Human K14 Keratin Gene in Transgenic Mice". This publication discloses that Vassar et al. used a plasmid containing a K14 keratin promoter and a neuropeptide substance P and determined the expression of the plasmid and neuropeptide substance P in the tail skin of transgenic mice.

Vassar et al. in *Gene & Development*, Volume 5, pages 714–727, (1991) disclose "Transgenic Mice Provide New Insights into the Role of TGF-α During Epidermal Development and Differentiation". This publication discloses the construction of transgenic mice using a plasmid which contains the K14 keratin promoter and the TGF-α gene. Vassar et al. disclose that the TGF-α gene belongs to the epidermal growth factor family of proteins and shows structural homology with the epidermal growth factor. These transgenic mice showed gross phenotypic abnormalities in their skin including flaky outer epidermal layers with stunted hair growth and wrinkling. The plasmid used to create this transgenic mouse also included human growth hormone fusion gene.

Patil et al. in *Neuron*, Volume 2, pages 347–447, March 1990, disclose "Specific Neuronal Expression of Human Nerve Growth Factor Receptors in the Basal Forebrain and Cerebellum of Transgenic Mice". Patil et al. employed a cosmid clone containing the entire NGF receptor gene. Introduction of the human NGF receptor gene into the mouse germ line resulted in significant levels of expression in specific cells in both the peripheral and central nervous systems. The NGF receptor gene and the NGF gene are distinct genetic material.

Borrelli et al. in *Proceedings of the National Academy of Science*, Volume 89, pages 2764–2768, April 1992, disclose "Pituitary Hyperplasia Induced by Ectopic Expression of Nerve Growth Factor". Borrelli et al. fused nerve growth factor cDNA to rat prolactin promoter to induce its ectopic expression in pituitary lactotrophs of transgenic mice.

Federoff et al. in *Proceedings of the National Academy of Science, USA*, Volume 89, pages 1636–1640, March 1992, disclose "Expression of Nerve Growth Factor in Vivo from a Defective Herpes Simplex Virus-1 Vector Prevents Effects of Axotomy on Sympathetic Ganglia". This publication teaches that rat nerve growth factor packaged into a herpes simplex virus-1 particle after axotomy of sympathetic superior cervical ganglion prevented a decline in the tyrosine hydroxylase level which is generally required for maintenance of the noradrenergic neurotransmitter system.

Edwards et al. in the *Cell*, Volume 58, pages 151–170, Jul. 14, 1989, disclose "Directed Expression of NGF to Pancreatic β Cells in Transgenic Mice Leads to Selective Hyperinnervation of the Islets". Edwards et al. showed a selective increase the expression of NGF in pancreatic β cells by creating a hybrid gene that contained a rat insulin promoter fused to mouse NGF cDNA followed by an intron and transcriptional terminator from the SV40 virus.

PCT Publication WO 93/00909 is directed to a method of treating neurotrophin-expressing tumors by administering a sequence complementary to at least a portion of a RNA transcript of brain-derived neurotrophic factor gene.

During development of the vertebrate nervous system up to half of all neurons generated undergo a process of naturally occurring cell death (See Ard, M. D., Morest, D. K. (1984). Cell death during development of the cochlear and vestibular ganglia of the chick. *Intl. J. Dev. Neurosci.* 2, 535–547; and Oppenheim, R. W. (1991). Cell death during development of the nervous system. *Ann. Rev. Neurosci.* 14, 453–501).

Neuronal death typically occurs shortly after neurons being making functional connections within their target field. Survival during this period of innervation is thought to be dependent on the synthesis by the target tissue of a limited quantity of neurotropic substances. (See Thoenen, H. and Barde, Y. A. (1980). Physiology of nerve growth factor. *Physiol. Rev.* 60, 1284–1334; Oppenheim, R. W. (1989). The neurotrophic theory and naturally occurring motoneuron death. Trends in Neurosci. 12, 252–255; and Davies, A. M., Larmet, Y., Wright, E., Vogel, K. S. (1991). Coordination of trophic interactions by separate developmental programs in sensory neurons and their target fields. *J. Cell Sci.* 15, 111–116)).

The competition for- target field-derived neurotrophic factors is though to serve at least two functions: to ensure that an appropriate number of synaptic contacts are made at the target and to eliminate inappropriate neuronal projections. (See Oppenheim, R. W. (1981). Neuronal death and some related phenomena during neurogenesis. In *Studies in Developmental Biology* (ed. W. M. Cowan) p 74–133. Oxford University Press; and Cowan, W. M., Fawcett, J. W., O'Leary, D.D.M., and Stanfield, B. B. (1984). Regressive events in neurogenesis. Science 225, 1258–1265)).

This concept is referred to as the neurotrophic hypothesis and predicts that the number of neurons in the adult could be increased if a higher concentration of neurotrophic factor(s) was available during the critical time when synaptic contacts are being established.

Nerve growth factor (NGF) is a prototypical target-derived neurotrophic substance that has been shown to be essential for the survival and differentiation of neural crest-derived sensory neurons, sympathetic neurons, and forebrain cholinergic neurons. (See Levi-Montalcini, R. and Booker B. (1960). Destruction of the sympathetic ganglia in mammals by an antiserum to a nerve-growth protein. *Proc. Natl. Acad. Sci. U.S.A* 46, 384–391 and Hefti, F. (1986) *J. Neurosci.* 6, 2155–2161; Williams, L. R., Varon, S., Peterson, G., Wictorin, K., Fischer, W., Bjorklund, A. & Gage, F. H. (1986). *Proc. Natl. Aced. Sci. U.S.A.* 83, 9231–9235).

The role of NGF in neuron survival is supported by numerous studies that have utilized both tissue culture and in vivo approaches in which NGF peptide or NGF antibodies were applied. (See Levi-Montalcini and Booker, 1960, supra; Johnson, E. M., Gorin, P. D., Brandeis, L. D., Pearson, J. (1980). Dorsal root ganglion neurons are destroyed by exposure in utero to maternal antibody to nerve growth factor. *Science* 210, 916–918; Barde, Y. A., Edgar, D., Thoenen H. (1980). Sensory neurons in culture: Changing requirements for survival factors during embryonic development. *Proc. Natl. Acad. Sci. U.S.A.* 77, (1980) 1199–1203; Hamburger, V. and Yip, H. W. (1984). Reduction of experimentally induced neuronal death in spinal ganglia of the chick embryo by nerve growth factor. *J. Neurosci.* 4, 767–774). Sympathetic and certain sensory neurons can be reduced by exogenous NGF whereas anti-NGF antibodies eliminate these neurons.

During development of skin, NGF is expressed by target cells of the presumptive epidermis and dermis. (See Davies, A. M., Bandtlow, D., Heumann, R., Korsching, S., Rohrer, H., and Thoenen, H. (1987). Timing and site of nerve growth factor synthesis in developing skin in relation to innervation and expression of the receptor. *Nature* 326, 353–358).

Target-field synthesis of NGF coincides with the arrival of axons to the epidermis, though the onset of expression as well as the concentration of NGF are independent of innervation. (See Rohrer, H., Heumann, R., Thoenen, H. (1988). Synthesis of nerve growth factor (NGF) in developing skin is independent of innervation. *Dev. Biol.* 128, 240–244; and Harper, S. J., and Davies, A. M. (1990). NGF mRNA expression in developing cutaneous epithelium related to innervation density. *Development* 110,515–519). Thus, cells of the target field appear to control the onset and level of NGF gene expression.

In mouse whisker pad skin, time course studies of innervation have shown that by embryonic day 11 (E11) axons have grown out to the skin and NGF mRNA expression has begun. (See Davies et al., 1987, supra). NGF continues to rise until E14 and then falls sharply by E15. The decrease in NGF concentration coincides with the onset of death of nearly half of the neurons in the trigeminal ganglion.

As skin innervation proceeds, the embryonic epithelium begins the transformation from a two-cell layer, undifferentiated periderm to a multilayer, stratified epidermis. (See Schweizer, J., and Winter, H. (1982). Keratin polypeptide analysis in fetal and in terminally differentiating newborn mouse epidermis. *Differentiation* 22, 19–24; and Kopan, R. and Fuchs, E. (1989). A new look into an old problem: Keratins as tools to investigate determination, morphogenesis, and differentiation in skin. *Genes and Devel.* 3, 1–15).

The differentiation of the epidermis is marked by the expression of epidermal specific genes, one of the earliest being the gene encoding the keratin intermediate filament protein K14. The onset of K14 gene expression in mouse skin occurs at approximately E14-E15 (see FIG. 1(*b*), beginning as NGF concentration is declining.

Heretofore there has been no convenient method to investigate how target-derived NGF affects neuron survival and development of the peripheral nervous system or provide a practical model for testing drug candidates for the treatment of neurodegenerative disorders of the brain such as Parkinson's syndrome and Alzheimer's disease.

The present invention overcomes the deficiency by providing transgenic mice that manufacture increased levels of NGF in the basal keratinocytes of the skin and exhibit hyperinnervation.

DISCLOSURE OF THE INVENTION

The invention provides a transgenic mouse whose somatic and germ cells contain and express a gene encoding for nerve growth factor. The gene exhibits hyperinnervation in the mouse, and has been introduced into a mouse or an ancestor of the mouse at an embryonic stage. The NGF gene is operatively linked to a human K14 keratin promoter and enhancer region.

The invention also provides for a mouse wherein the NGF gene has been introduced into an ancestor if said mouse at an embryonic stage by microinjection.

In an additional embodiment, the mouse nerve growth factor is further operatively linked to the human growth hormone gene.

The invention provides for a mouse which has a phenotype characterized by hyperinnervation of the skin, hypertrophy of trigeminal ganglion and enlargement of the superior cervical sympathetic and dorsal root ganglia.

Advantageously, the present invention provides a method of producing the transgenic mouse which overexpresses nerve growth factor which comprises (a) providing a mouse nerve growth factor gene operatively linked to a human K14 keratin promoter and enhancer region functional in said mouse;

(b) introducing said gene into a mouse embryo;

(c) transplanting said embryo into a pseudopregnant mouse; and (d) allowing said embryo to develop to term.

Furthermore, the invention provides a method of testing the efficacy of drugs in treating neurodegenerative disorders comprising administering said drug to a mouse according to the invention, and determining the behavioral effects and tissue changes of said drug on said mouse.

BRIEF DESCRIPTION OF DRAWINGS

FIGS. 1a, b, c.

FIGS. 2a, b.

FIGS. 3a–d: FIG. 3 shows cellular expression of the K14-NGF transgene in skin from A-56 F1 transgenics was examined by in situ hybridization. Basal cells (arrows) in whisker pad epidermis, FIG. 3(a), and vibrissa, FIG. 3(c), of control animals had silver grain density at background levels. A-56 F1 transgenic mice had a greater labeling density of whisker pad basal cells, FIG. 3(b) (arrows), and vibrissa, FIG. 3(d).

FIG. 4 shows expression of K14-NGF causes hyperinnervation of skin. Skin from dorsum, (FIGS. 4a and 4b) and whisker pad (FIG. 4c and 4d) was processed for paraffin histology and sections stained with hematoxylin and eosin. Control skin (FIG. 4a and 4c) show few apparent neuron bundles whereas A-56 F1 transgenic skin (FIG. 4b and 4d) shows numerous, enlarged fiber bundles.

FIGS. 5a–d: FIG. 5 shows immunolabeling of transgenic skin reveals a hyperinnervation of sensory and sympathetic neurons. To verify that the fiber bundles in the skin were composed of neuronal processes, frozen sections of whisker pad skin from control (FIG. 5a) and A-56 F1 transgenics (FIG. 5b) were immunolabeled with an anti-neurofilament 150 antibody followed by incubation with a goat anti-rabbit FITC conjugated secondary. A significant increase in the number of fibers and bundles was seen in an equivalent region of A-56 transgenic skin (FIG. 5b). A-56 skin contained sympathetic fibers, sections were immunolabeled with an anti-TH antibody followed by a biotinylated goat-anti rabbit secondary processing with DAB (FIG. 5c). A-56 F1 transgenics labeled with anti-CGRP followed by a biotinylated goat-anti rabbit secondary antibody are shown in FIG. 5d.

FIGS. 6a, b: FIG. 6 shows expression of K14-NGF causes enlargement of the trigeminal and superior cervical ganglia. Trigeminal ganglia (FIG. 6a) and superior cervical ganglia (FIG. 6b) were removed from control A-48 F1, and A-56 F1 mice.

STATEMENT OF DEPOSIT

The plasmid containing k14-NGF-hGH has been deposited with the American Type Culture Collection under the terms of the Budapest Treaty and is available as Accession No. 69423.

DESCRIPTION OF THE INVENTION

The present invention provides transgenic mice that manufacture increased levels of nerve growth factor (NGF) in the basal keratinocytes of the skin.

The mice are obtained by making a fusion gene construct in which the human K14 keratin promoter and enhancer region was linked to mouse NGF cDNA.

To increase the expression of the transgene, a region from the human growth hormone gene may, in a preferred embodiment, be added to the construct. Production of nerve growth factor in the epidermis of these mice was found to result in a profound hyperinnervation of the peripheral nervous system, i.e. skin has increased nerve fibers, the trigeminal sensory, the superior cervical sympathetic, and the dorsal root ganglia were markedly enlarged.

The nerve growth factor expressing transgenic mice of the present invention are valuable to researchers that study the role of nerve growth factor and other neurotrophic factors in the development and function of the nervous system, and in the study of neurodegenerative disorders of the brain such as Parkinson's syndrome and Alzheimer's disease.

To investigate the role of NGF in the development of the peripheral nervous system and skin innervation, the human K14 gene promoter was used to drive the expression of the NGF cDNA in basal keratinocytes. Results show that target-derived overexpression of NGF has profound effects on the level of skin innervation and neuronal survival.

Below is a more detailed outline of experimental procedure. NGF cDNA was linked to the promoter and enhancer regulatory regions of the human keratin 14 gene. The K14-NGF fusion gene was expressed at approximately embryonic day 14, the time at which endogenous NGF levels begin to decline and programmed neuronal death begins. In situ hybridization of skin of K14-NGF transgenics had increased levels of NGF mRNA in the basal cells of the epidermis and associated hair follicle structures. The increase in target derived NGF mRNA was correlated with a hypertrophy of peripheral sensory and sympathetic nerves, hyperinnervation of the skin, and a 26–117% increase in the number of primary sensory neurons in the trigeminal ganglion.

These results demonstrate that the level of NGF production by the target tissue dictates the level of neuron survival, and in so doing, influences the distribution and number of neurons in the adult.

Expression of K14-NGF in Skin of Transgenic Mice

Figure 1A:
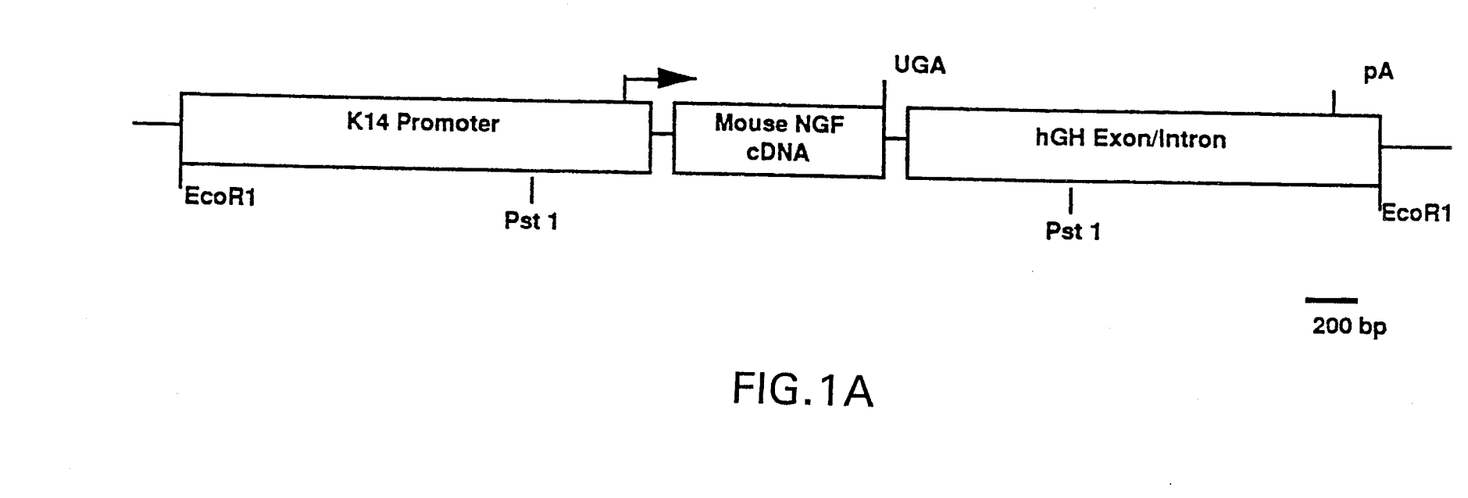
(FIG. 1(a) shows the K14-NGF fusion gene contains the mouse NGF cDNA cloned downstream from the human epidermal K14 gene promoter and enhancer sequences.
Figure 1B:
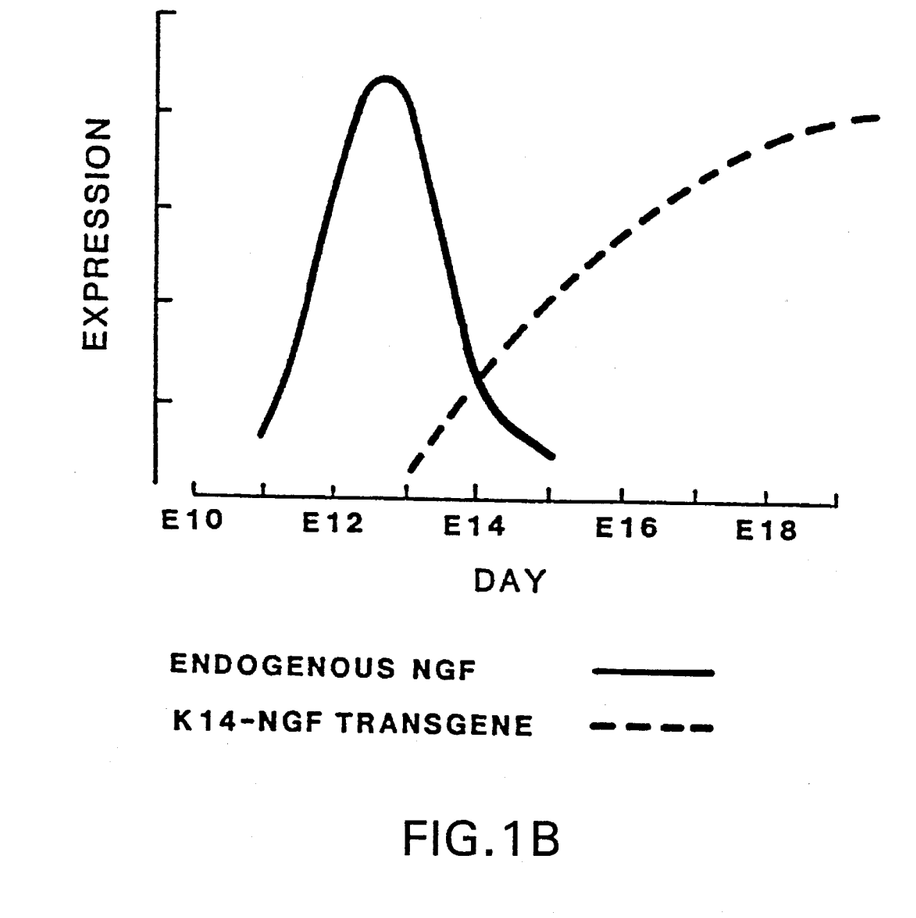
FIG. 1(b) shows a schematic depicting the onset of NGF expression by E11, and its rise and fall at E15.

NGF was overexpressed in the epidermis of transgenic mice using a fusion gene construct in which the human epidermal K14 keratin promoter and enhancer sequences were linked to a mouse NGF cDNA (FIG. 1a). The K14 promoter has previously been shown to direct high level of expression of various transgenes to basal keratinocytes of the epidermis. (See Vassar, R., Rosenberg, M., Ross, S., Tyner, A. & Fuchs, E. (1989). Tissue-specific and differentiation-specific expression of a human K14 keratin gene in transgenic mice. *Proc. Natl. Acad. Sci.* 86, 1563–1567; and Vassar, R., Coulombe, P. A., Degenstein, L., Albers, K. & E. Fuchs (1991). Mutant keratin expression in transgenic mice causes marked abnormalities resembling a human genetic skin disease. *Cell* 64, 365–380).

The rationale in designing the K14-NGF construct is based on the temporal overlap of NGF down-regulation with the initiation of K14 expression, i.e., as the concentration of target derived NGF beings to fall and neuronal cell death commences (E14-E15, see FIG. 1(b)), the K14-NGF transgene turns on, producing elevated levels of NGF during the critical period of cell death and thereafter in the adult (FIG. 1b).

Figure 1C:
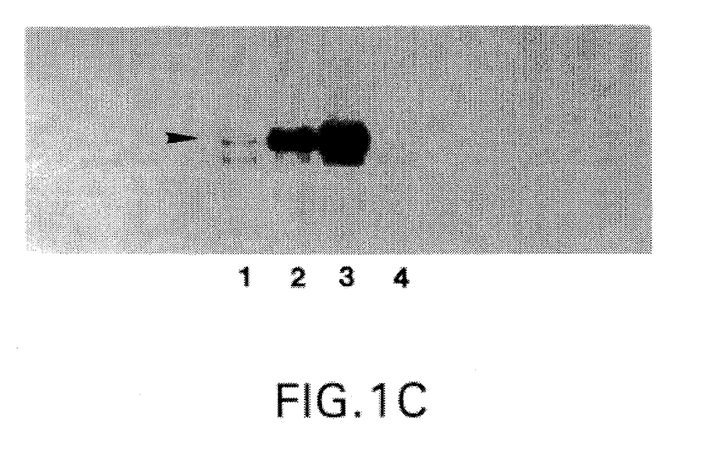
FIG. 1(c) shows mice screened for the transgene by Southern hybridization of DNA isolated from tail samples obtained three to four weeks after birth. Blots were probed using a $^{32}$P-labeled DNA sequence complementary to the mouse NGF cDNA.

Three founder mice have been isolated that express the transgene (FIG. 1c). Founder A-39 (FIG. 1c, lane 1) and founder A-56 (lane 3) were smaller and exhibited a lower rate of weight gain when compared to their nontransgenic siblings, whereas founder A-48 was normal in size. F1 offspring of founder A-56 also exhibited reduced weight gain. Founder A-39 has not generated transgenic offspring, though approximately eighty offspring have been screened. The A-56 transgenics also had delayed eye opening (at least 2–3 days later than nontransgenic siblings) and frequently exhibited a "squinty" appearance. This phenotype does not appear to be due to an increase in light sensitivity since even under low level lighting they retained a squinting appearance.

Figure 2A:
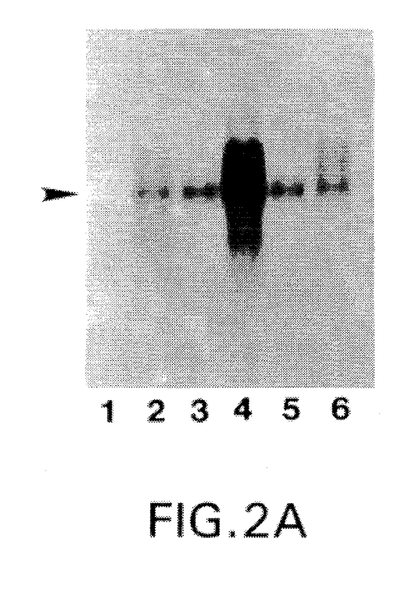
FIG. 2(a) examines the expression level of the K14-NGF transgene for transgenic mouse lines. Shown is a 3 d exposure, FIG. 2(a) and a 10 d exposure, FIG. 2(b), of the same filter.

The relative level of K14-NGF expression in the three founders was determined using Northern hybridization analysis of total RNA isolated from full thickness skin (FIG. 2). Nontransgenic control skin samples (FIG. 2, lane 1) had a single faint band hybridizing with the radiolabeled NGF probe at approximately 1.3 kb, a size corresponding to the endogenous RNA transcript.

RNA samples isolated from the A-39 (lane 2), A-48 (lane 3), and A-56 (lane 4) skin contained, in addition to the endogenous transcript, a 1.9-kb band that corresponded to the predicted size of the K14-NGF transcript. Line A-39 and A-48 had comparable levels of transgene expression whereas expression in the A-56 line was significantly higher. Previous studies using the K14 promoter and enhancer region to express other transgenes of interest have shown transgene expression restricted to stratified, keratinized tissues such as skin, tongue, esophagus, and forestomach.

Figure 2B:
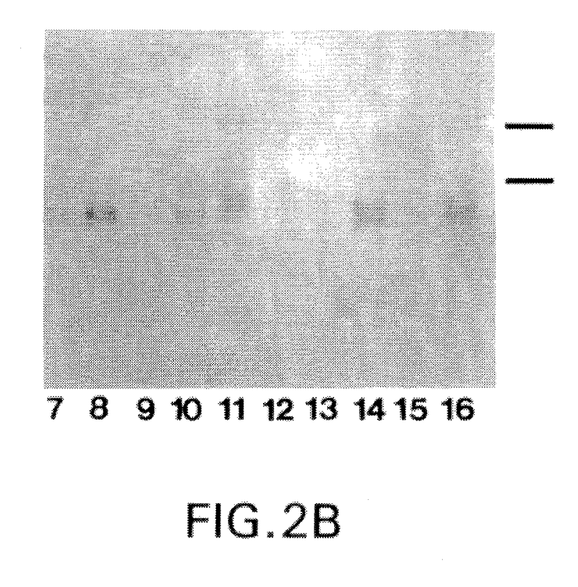
FIG. 2(b) examines the tissue specificity of K14-NGF expression.
Figure 3A:
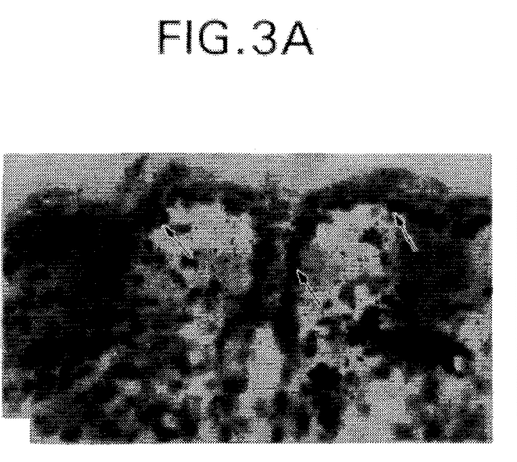
Figure 3B:
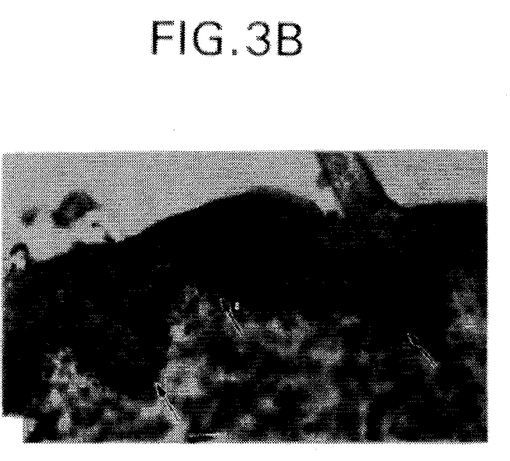
Figure 3C:
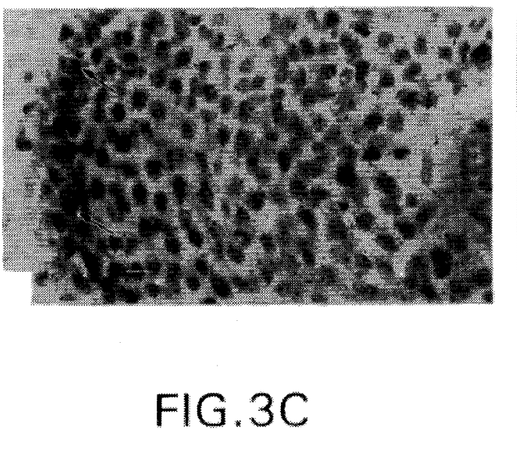
Figure 3D:
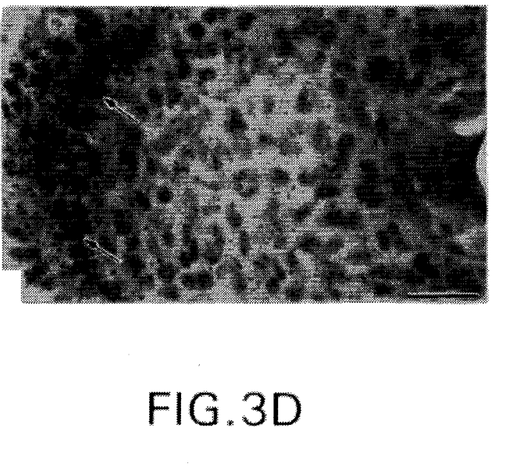

To verify that the tissue distribution of K14-NGF expression was comparable, RNA was analyzed from tongue, brain, heart, liver, and kidney of an A-56 F1 transgenic and nontransgenic control. Expression of the K14-NGF transgene was restricted to the keratinized epithelium samples examined, skin (FIG. 2, lane 5) and tongue (lane 6). The endogenous NGF transcript was detectable in skin (lanes 5 and 11), tongue (lanes 6 and 12), brain (lanes 7 and 13), heart (lanes 8 and 14), and kidney (lanes 10 and 16) of both the control and transgenic tissues. Liver tissues (lanes 9 and 15) showed no evidence of NGF expression.

Cellular expression of the K14-NGF transgene was examined using in situ hybridization on sections of whisker pad skin, a region known to have a high level of innervation (FIG. 3). A $^{35}$S-labeled cRNA probe specific for the mouse NGF mRNA was hybridized to skin sections of 4 week-old K14-NGF transgenics and non-transgenic siblings and processed for autoradiography. Few autoradiographic grains were observed in the control skin (FIG. 3a) whereas the K14-NGF skin showed dense hybridization in the epidermal basal cell layer with decreasing intensity in suprabasal layers (FIG. 3b). Dense hybridization was also found in epidermal cells of the outer root sheath of hair and vibrissa follicles of transgenic mice (FIG. 3d), but not in the corresponding areas of nontransgenic (FIG. 3c). The epidermal and hair follicle distribution of hybridization is consistent with the known expression pattern of the K14 keratin (Schweizer and Winter, 1982; Kopan and Fuchs, 1989).

Histological Examination of NGF Levels

Figure 4A:
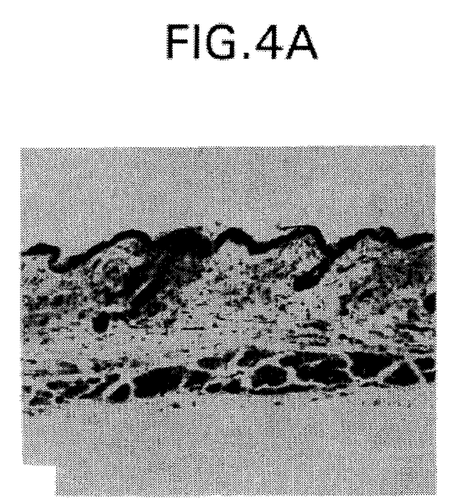
Figure 4B:
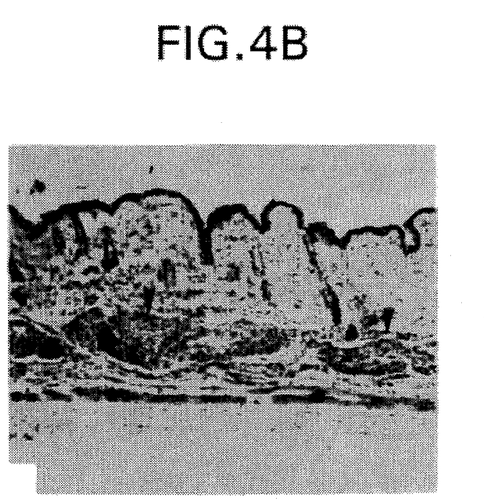

To determine whether the increased level of NGF mRNA in the transgenic epidermis was processed into functional NGF peptide, the skin of the transgenics was examined for evidence of increased neuronal survival. Histological examination of skin from various regions of the body (dorsum, ventral, tail, ear locations) revealed an increase in nerve processes and an abundance of large nerve bundles coursing throughout the papillary and reticular layers of the dermis (FIG. 4a, control; 4b, transgenic).

Figure 4C:
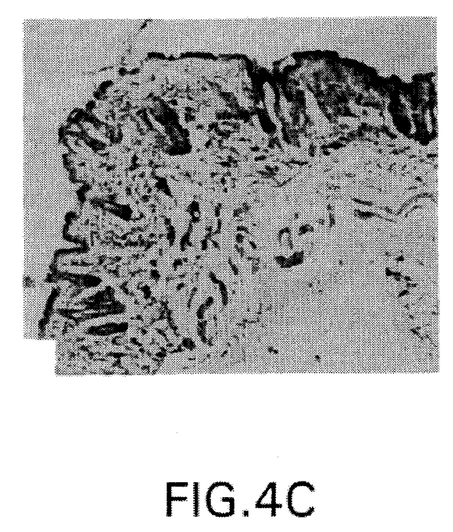
Figure 4D:
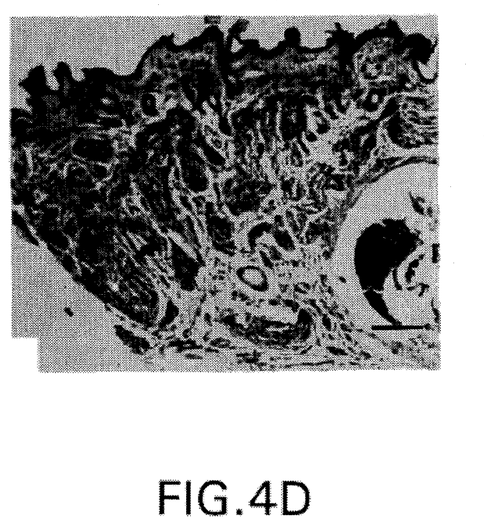

To confirm that these structures were composed of neuronal processes, whisker pad skin from A-56 F1 mice was immunolabeled with an antibody directed against the 150 Kd neurofilament protein (FIG. 4c, control; 4d, transgenic). In control mice, neurofilament positive fibers and bundles were evident in the reticular and deep layers of the dermis. Occasional small positive fibers could also be found penetrating the lower layers of the epidermis and in association with hair follicle and vibrissa structures.

A striking increase in the density and size of neuronal processes was apparent in skin of A-56 transgenics (FIG. 4d). Hyperinnervation was clearly evident in the papillary and reticular layers of the dermis as well as around hair follicle structures. Hyperinnervation was also apparent in skin of A-48 F1 mice, though at a reduced level than in the A-56 transgenics.

Two primary sources of axons for the observed whisker pad hyperinnervation are sensory neurons originating in the trigeminal ganglion and sympathetic postganglionic fibers arising from the superior cervical ganglion. As a first step in determining the contribution from these two sources, immunocytochemistry was performed using antibodies directed against the neurotransmitter calcitonin gene related peptide (CGRP), for identification of sensory neurons and the catecholamine-synthesizing enzyme tyrosine hydroxylase (TH), for identification of postganglionic sympathetic axons. (See Gibbins, I. L., Furness, J. B., Costa, M., MacIntyre, I., Hillyard, C. J. and Girgis, S. (1985). Colocalization of calcitonin gene-related peptide-like immunoreactivity with substance P in cutaneous, vascular and visceral sensory neurons of guinea pigs. *Neurosci. Lett.* 57, 125–130).

CGRP is enriched in sensory nerves projecting to hair follicles and as free endings in the epidermis. (See Kruger, L. Silverman J. D., Mantyh P. W., Sternini, C., Brecha, N. C. (1989). Peripheral patterns of calcitonin gene-related peptide general somatic sensory innervation: cutaneous and deep terminations. *J. Comp. Neurol.* 280, 291–302; and Shotzinger, R. J., and Landis, S. C. (1990). Postnatal development of autonomic and sensory innervation of thoracic hairy skin in the rat. *Cell Tissue Res.* 260, 575–587).

Figure 5A:
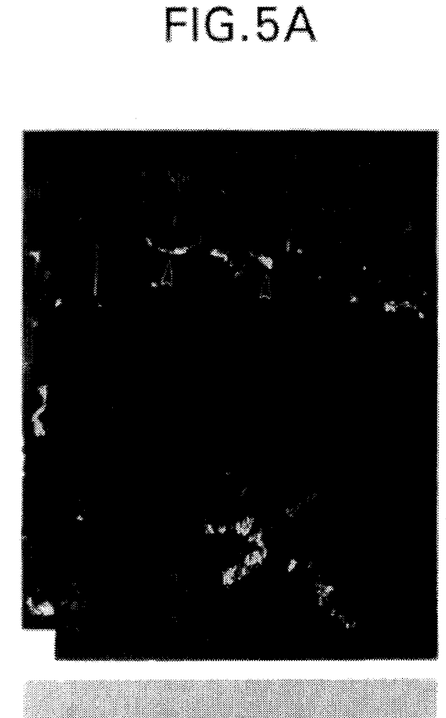
Figure 5B:
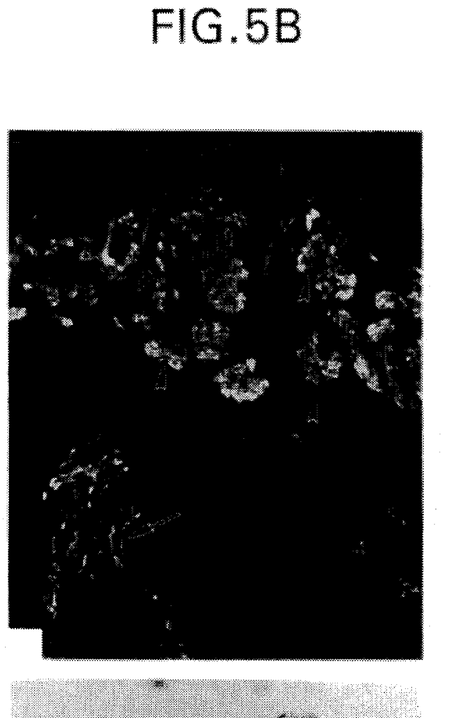

Though CGRP staining has been reported in sympathetic ganglion, it is thought to represent afferent input, not CGRP production by ganglionic neurons. In control skin (FIG. 5a), few CGRP-positive fibers could be identified. In contrast, the K14-NGF transgenic skin had numerous small and large bundles of CGRP-labeled fibers throughout the dermis, particularly in regions beneath the epidermis where abundant axons terminations occur (FIG. 5b).

Figure 6A:
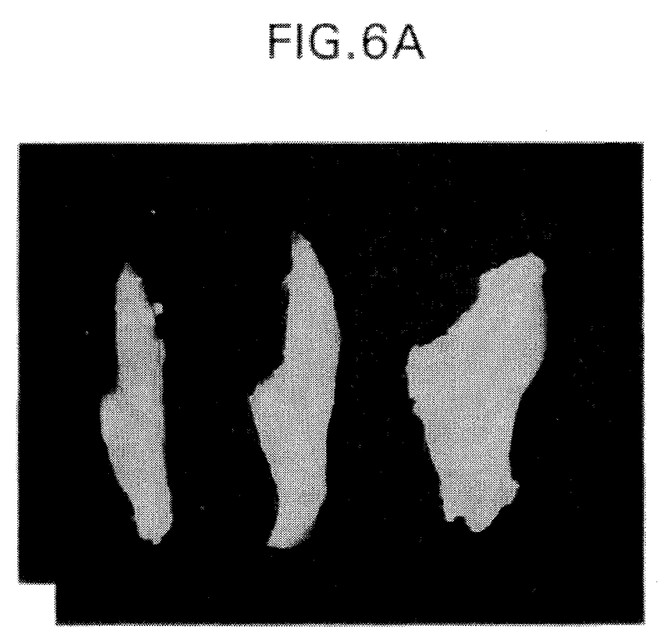
Figure 6B:
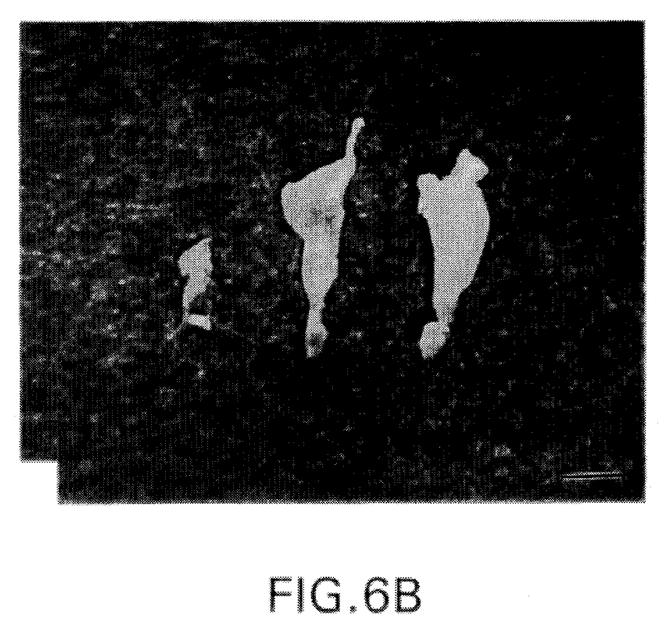

Sympathetic innervation of transgenic skin was enhanced as shown by an increase in TH-immunoreactive fibers (FIG. 6c, control; 6d, transgenic). Much of the increased TH labeling was on fiber bundles in the upper regions of the dermis that also labeled for CGRP. TH-positive fibers appeared different from CGRP positive fibers however, in being thin, with numerous swellings. CGRP fibers were thicker and more uniform. Further distinction between CGRP labeled and TH labeled fibers was found in examination of Merkel cells of vibrissa structures. (See Nurse, C. A., Mearow, K. M., Homes, M., Visheau, B., and Diamond, J. (1983). Merkel cell distribution in the epidermis as determined by quinacrine fluorescence. *Cell Tissue Res.* 228, 51–54). Sensory, but not sympathetic neurons, recognize and associate with Merkel cells. (See Vos, P., Stark, F., and Pittman, R. N. (1991). Merkel cells in vitro: Production of nerve growth factor and selective interactions with sensory neurons. *Dev. Biol.* 144, 281–300). In transgenic and control samples only CGRP labeled fibers could be found associated with Merkel cells of the whisker follicle whereas no TH labeling was evident.

It was found that TH and CGRP synthesis is enhanced by NGF. No difference in TH-labeling could be discerned between the control and transgenic samples in the deep dermis. Few TH-immunoreactive fibers could be found in the deep dermis and these fibers were frequently associated with blood vessels that were adjacent to the underlying muscle layer, a location consistent with their sympathetic nature.

It was also found that NGF induces hypertrophy of trigeminal ganglion. The availability of elevated NGF peptide to neurons in the epidermal target field of the transgenics was further indicated by a striking hypertrophy of the trigeminal ganglion and the branches emanating from it. Cell counts made of ganglia isolated from three A-56 F1 transgenics had values that ranged from 26 to 117% greater than nontransgenic age-matched controls (Table 1 below). The hypertrophy of the trigeminal ganglion was also reflected by the enlargement of the primary branches of the trigeminal nerves. In the maxillary division of the trigeminal nerve dissected from control and transgenic samples, the transgenic nerve bundle (branch) is clearly larger than the control.

TABLE 1

| Case Number | Age | Number of Neurons | Percent Difference |
|---|---|---|---|
| 0401 Non-transgenic | 24 d | 26,054 | 55 |
| 0401 K14-NGF transgenic | 24 d | 40,285 | |
| 0527 Non-transgenic | 29 d | 26,493 | 117 |
| 0527 K14-NGF transgenic | 29 d | 57,767 | |
| 0513 Non-transgenic | 36 d | 28,867 | 26 |
| 0513 K14-NGF transgenic | 36 d | 36,562 | |

A transgenic mouse model system was used to study the role of target field-derived NGF in development of the peripheral nervous system. Elevation of the production of NGF by the epidermal target tissue caused a dramatic increase in neuronal survival as evidenced by a striking hyperinnervation of the skin and hypertrophy of the trigeminal ganglia. Both sensory and sympathetic neurons in the transgenic skin appeared to be rescued by the increased NGF production as evidenced by enhanced CGRP- and TH-immunoreactivity. That both sensory and sympathetic neuron populations had increased survival is consistent with the known dependence of these cells on NGF. Sensory neurons are most dependent during embryonic development (shortly before birth) whereas sympathetic neurons require NGF within a 304 week period after birth. (See Levi-Montalcini and Booker, 1960, supra; Johnson et al., 1980, supra).

Since expression of the K14-NGF transgene begins at E14-E15, rises, and continues at a steady level in the adult, both sensory and sympathetic neurons would be exposed to elevated NGF at critical times in their development. Nerve terminals of both sympathetic and sensory neurons would presumably have access to a greater amount of NGF produced by the transgenic epidermis and transport it from the skin to cell bodies. Both sensory and sympathetic nerves have been shown to take up labeled NGF and transport it retrogradely. (See Hamburger, V., Brunso-Bechtold, J. K., Yip, J. W. (1981). Neuronal death in the spinal ganglia of the chick embryo and its reduction by nerve growth factor. *J. Neurosci.* 1, 60–71; and Stockel, L., Schwab, M. E., Thoenen, H. (1975). Comparison between the retrograde axonal transport of nerve growth factor and tetanus toxin in motor, sensory and adrenergic neurons. *Brain Res.* 89, 1–16).

It was found that TH and CGRP can be upregulated by NGF. During normal development, the maximum number of cells in the trigeminal ganglia are found at E13 (see FIG. 1(b). (See Davies, A. M. and A. Lumsden, (1984). Relation of target encounter and neuronal death to nerve growth factor responsiveness in the developing mouse trigeminal ganglion. *J. Comp. Neurol.* 223, 124–137). These values are twice that measured at postnatal day four, a result consistent with the neurotrophic theory that up to half of all sensory neurons produced during development die as the animal matures. The trigeminal ganglia of mice expressing the K14-NGF transgene had up to double the number of cells than present in control mice.

Since the addition of exogenous NGF is known to block sensory neuron death, the most likely explanation for the increased cell number in the transgenic ganglia is that the supernormal levels of NGF generated by K14NGF transgene expression in the target prevented cell death. Another possibility is that additional neurogenesis was induced by increased levels of NGF. Recent studies have suggested that NGF can act as a mitogen in the anterior pituitary and as a meiotic growth factor during spermatogenesis. (See Borrelli, E., Sawchenko, P. D. Evans, R. M. (1992). Pituitary hyperplasia induced by ectopic expression of nerve growth factor.

*Proc. Natl. Acad. Sci. U.S.A.* 89, 2764–2768; and Parvinen, M., Pelto-Huikko, M., Soder, O., Schults, R., Kaipia, A., Mali, P., Toppari, J., Hakovirta, H., Lonnerberg, P., Ritzen, E. M., Ebendal, T., Olson, L., Hokfelt, T., Persson, H. (1992). Expression of B-nerve growth factor in rat seminiferous epithelium: specific function at the onset of meiosis. J. Cell Biol. 117, 629–642).

However, if NGF does exert a mitogenic effect on peripheral neurons it must occur prior to the first four-to-six weeks of postnatal development (the age at which animals were examined), since we observed no mitotic figures in the trigeminal ganglia despite examination of over 4000 cells/ganglia. In addition, the K14-NGF transgene is active after the period of normal cell birth and at a time when sensory neurons have completed their migration and extended processes into the periphery. Typically, sensory neurons that are this highly differentiated do not undergo neurogenesis. (See Pannese, E. (1974). *Adv. Anat. Cell Biol.* 47, 1).

In addition to the apparent sensory neuron hyperinnervation, some of the increased innervation resulted from increased survival of NGF responsive sympathetic postganglionic neurons that innervate blood vessels, sweat glands, and the erector pili muscles associated with hair follicles. Sympathetic neuronal cell bodies that innervate the whisker pad skin are located in the superior cervical ganglion, a structure that was also enlarged in the K14-NGF transgenics. The increase in tyrosine hydroxylase immunoreactivity was restricted to the fiber bundles in the superficial portion of the dermis. Blood vessels which normally receive a few intensely stained TH-positive fibers appeared to have the same low level of sympathetic innervation in the transgenic mice. These blood vessels are well removed from the basal keratinocytes expressing the NGF transgene suggesting the hyperinnervation is supported only for those structures near the site of NGF overproduction.

The hyperinnervation of a target may be dependent on factors other than increased expression of NGF. Merkel cells are abundant in vibrissae structures and receive sensory input. In the K14-NGF transgenics, a large increase in the number of CGRP-positive fibers projecting to these cells was found. No TH-positive fibers were seen projecting to these cells even though large numbers of TH-positive axons were seen in nerve bundles immediately adjacent to the vibrissae. These results agree with experiments reported by Edwards et al. in which the rat insulin promotor was utilized to overexpress the NGF cDNA in islet cells of the pancreas. (See Edwards, R. H., Rutter, W. J., Hanahan, D. (1989). Directed expression of NGF to pancreatic β cells in transgenic mice leads to selective hyperinnervation of the islets. *Cell* 58, 161–170).

Hyperinnervation of the pancreas was observed, though the sole source of innervating fibers appeared to be sympathetic postganglionic neurons. No apparent effect of increased NGF was observed on sensory fibers. From this finding it was proposed that the selective affect on sympathetic axons was due to unidentified cofactors that supported hyperinnervation of the sympathetic but not sensory axons. This type of mechanism may have relevance to another transgenic mouse expression study in which the prolactin promotor was utilized to target NGF expression to the anterior pituitary, a tissue not normally innervated. Though an increased amount of NGF was synthesized, the anterior pituitary was not innervated, i.e., NGF did not induce innervation of an inappropriate target.

The expression paradigm used has allowed an examination of the neurotrophic hypothesis and the effect of increased target-derived NGF on cell survival. The results demonstrate that the increased expression of NGF in the developing epidermis can inhibit, if not completely block, neuron cell death. Moreover, the increase in the number of surviving neurons was independent of changes in the volume of the skin or number of cells in the target tissue (in this case the skin) indicating the trophic factor alone can regulate the number of surviving axons.

These results support the neurotrophic hypothesis and specifically demonstrate that the skin, by regulating the timing and amount of NGF expression independent of innervation plays a central role in the development of the peripheral nervous system.

EXAMPLES

EXAMPLE 1

Construction of K14-NGF transgene and introduction into mice. Plasmid pKS-NGF (a gift from R. Edwards, U.C.L.A.) was cut with Apa 1 (+230) and Pst 1 (+1027) to remove a 797 base pair fragment that encodes the NGF short transcript (Edwards et al., 1989). The overhanging ends of the Apa 1-Pst 1 NGF fragment were removed using mung bean nuclease and the fragment was gel purified and ligated into the BamHl cut, Klenow filled K14-hGH cassette vector (Vassar and Fuchs, 1991, supra). Dr. Elaine Fuchs (University of Chicago) provided the K14-hGH plasmid.

K14-hGH contains 2.1 kbp of 5' upstream sequence of the human K14 keratin gene and a 1.8 kbp intron containing sequence from the human growth hormone (hGH) gene. The hGH sequence serves to upregulate expression of the transgene and provides a polyadenylation signal. (See Sandgren, E. P., Luetteke, N. C., Palmiter, R. D., Brinster, R. L. & Lee, D. C. (1990). Overexpression of TGF alpha in transgenic mice: Induction of epithelial hyperplasia, pancreatic metaplasia, and carcinoma of the breast. *Cell*, 61, 1210–1135).

The 5-kbp EcoR1 k14-NGF-hGH fragment (FIG. 1a) was isolated on 0.8% Seaplaque agarose gel (FMC Corporation), extracted from the gel using glassmilk purification (Geneclean Bio 101), and run through a NACS column (Bethesda Research Laboratories).

The plasmid used to transfect mouse cells according to the present invention k14-NGF-hGH has been deposited with the American Type Culture Collection under the terms of the Budapest Treaty and is available as Accession No. 69423.

DNA was ethanol precipitated, resuspended in phosphate buffered saline at a concentration of 5 μg/ml, and injected into fertilized C3HB6 mouse (Harlan Laboratory Supplies) embryos. Injections and implantations were carried out using standard procedures. (See Hogan, B., Costantini, F. & Lacy, E. (1986). *Manipulating the Mouse Embryo: A Laboratory Manual* (Cold Spring Harbor Press, Cold Spring Harbor, N.Y.).

Mice were screened for the transgene using Southern hybridization analysis on DNA extracted from tail or by employing the polymerase chain reaction on DNA samples isolated from ear punches. For Southern hybridizations, 10 ug of DNA was digested with Pst 1, separated on an 0.7% agarose gel, transferred to nitrocellulose by blotting and probed with a random primed $^{32}$P-dCTP (New England Nuclear) labeled probe made to the full length NGF cDNA.

EXAMPLE 2

Analysis of mRNA expression by Northern hybridization. Northern analysis was performed on RNA that was isolated from various tissues using guanidium thiocyanate/ phenol/ chloroform extraction. (See Chomczynski, P. & Sacchi, N. (1987). Single-step method of RNA isolation by acid guanidinium thiocyanate-phenolchloroform extraction. *Analyt. Biochem.* 162, 156–159).

Fifteen micrograms of total RNA was resolved on a 1.2% agarose formaldehyde denaturing gel, transferred to Nytran membrane (Schleicher and Schuell) by blotting, baked 2 h in a vacuum oven at 80° C., and then hybridized to a $^{32}$P-dCTP labeled random primed probe made to the full length NGF cDNA.

EXAMPLE 3

In situ hybridization. $^{35}$S-labelled cRNA probes were generated by adding 1ug of linearized pKS-NGF plasmid (linearized with Sac 1 for an antisense probe and EcoR1 for a sense probe) to 2.5mM each ATP, CTP, GTP, 15 mM [$^{35}$S]UTP (New England Nuclear) and either T7 or T3 polymerase (Stratagene) to generate antisense and sense probes, respectively. Incubation was for 60 min at 40° C. in transcription buffer containing 50 mM MgCl$_2$, 20 mM spermidine, 20 mM Tris (pH 7.4) and 10 mM DTT. The solution was phenol:chloroformextracted and precipitated with ammonium acetate and 2.5 volumes of ethanol in the presence of 25 μg carrier tRNA.

For in situ hybridization, mouse whisker pad skin was dissected, immediately frozen on dry ice, cryostated at 10–20 μm, mounted onto Vectabond-coated slides (Vector Labs) and stored at −80° C. until hybridized. To hybridize, slides were brought to room temperature, fixed for 10 min in 4% paraformaldehyde, washed in diethyl pyrocarbonate (DEPC)-treated phosphate buffer, transferred to 0.25% acetic anhydride in 0.1 M TEA (pH 8/0) for 10 min at room temperature, dehydrated through a graded series of alcohols and defatted in chloroform. Sections were hybridized for 12–24 hr at 60° C. in a hybridization solution consisting of $1\times10^{TM}$ cpm/ml of $^{35}$-labeled cRNA probe, 50% formamide, 1X Denhardt's solution, 200 mMTris (pH 7.5), 10% dextran sulfate, 0.3 μg/ml salmon sperm DNA, 0.15 mg/ml tRNA, and 40 mM DTT. Slides were washed in 4×SSC (1×SSC= 0.15M NaCl, 0.015M sodium citrate, pH 7.0), incubated in 20 mg/ml ribonuclease A (Sigma) dissolved in 10 mM Tris-saline, and then washed through descending concentrations of SSC. The final wash was with 0.1×SSC at 37° C. for 1 hour. Sections were air-dried and placed in X-ray cassettes with Hyperfilm β-Max X-ray film (Amersham). Films were exposed for 3–7s and developed in Kodak D-19. Selected slides were dipped in Kodak NTB-2 liquid emulsion, air-dried and exposed to film. Emulsion dipped slides were developed in D19, fixed in Kodak rapid fixer, counterstained with hematoxylin/eosin or cresyl violet and coverslipped in Permount.

Skin sections from transgenic mice and nontransgenic siblings were processed in parallel. Controls for probe specificity included hybridization using a sense cRNA probe and pretreatment of tissue with RNase. Both of these conditions resulted in the absence of hybridization.

EXAMPLE 4

Cell counts of trigeminal neurons. Cell counts were obtained using the method of Coggelshall et al. (See Coggelshall, R. E., Chung, K., Greenwood, D., Hulsebosch, C. (1984). An empirical method for converting nucleolar counts to neuronal numbers. *J. Neurosci. Methods* 12, 125–132; Coggelshall, R. E., La Forte, R., and Klein, C. M. (1990). Calibration of methods for determining numbers of dorsal root ganglion cells. *J. Neurosci. Methods* 35, 187–194.).

This method is based on a determination of the number of neuronal nucleoli. Animals were placed under deep anesthesia and perfused transcardially with 4% paraformaldehyde in 0.1M phosphate buffer, pH 7.4. Trigeminal ganglia were removed and immersion fixed in 4% paraformaldehyde, dehydrated in alcohol, defatted and embedded in paraffin. Entire ganglia were serial sectioned at 6 μm and stained with hematoxylin and eosin. Every tenth section was examined at a total magnification of 400× and a drawing tube was used to trace the outline of the section and to demarcate the location of each sensory neuron containing a nucleoli. To compensate for neurons with two or more nucleoli, profiles of randomly selected neurons were reconstructed and the total number of nuclei per 100 neurons was determined. This provided a ration of nucleoli/neuron that was multiplied by the total neurons counted to obtain the total number of neurons per ganglion (Coggeshall et al., 1990, supra).

EXAMPLE 5

Immunohistochemistry. Tissue was immersed in fixative for 90 min., transferred to 20–30% sucrose in phosphate buffered saline (PBS) and incubated overnight at 4° C. Samples were cryostated at 10 μm, thaw-mounted onto Vectabond-coated glass slides and processed for immunocytochemistry.

Sections were incubated with primary antibody (diluted in PBS containing 1% normal goat serum and 0.3% Triton X-100), 18–24 h at 4° C. in a humidified chamber, rinsed in PBS for 30 min (3 changes), incubated in a secondary antisera consisting of appropriate fluorophore-conjugated IgG immunoglobulins (diluted in PGC with 0.3% Triton X-100; 1 h at room temperature), rinsed in PBS, and coverslipped.

Primary antibodies recognizing the following proteins were used: anti-150 Kd neurofilament protein (NF 150; 1:300 dilution; Chemicon), calcitonin gene related peptide (CGRP; 1:200 dilution; Chemicon), tyrosine hydroxylase (TH; 1:100 dilution; Chemicon).

Binding of the neurofilament antibody was visualized using anti-rabbit fluorocein isothiocyanate conjugated secondary antibody (Cappel Laboratories). Visualization of CGRP and TH immunoreactivity was achieved using avidin-biotin-peroxidase complex (ABC) kit from Vector Laboratories.

After primary antibody incubation, sections were washed twice in PBS (5 min. each) incubated in biotinylated goat-anti rabbit secondary antibody for 30 min., washed in PBS and incubated in the ABC complex for 30 min. following two PBS washes, immunoreactivity was visualized by incubation in 0.025% 3,3'-diaminobenzidine-4HCl (Aldrich) with 0.05% H$_2$O$_2$ and 1.5% nickel ammonium sulfate dissolved in 0.1M sodium acetate buffer, pH 6 for 7 minutes.

EXAMPLE 6

To test the efficacy of drugs in treating neurodegenerative disorders, a drug candidate is administered to a mouse according to the invention. The behavioral effects and tissue changes of the mouse are determined upon administration of the drug.

DETAILED DESCRIPTION OF THE DRAWINGS

FIG. 1 Transgene Construct and characterization of transgenic expression

FIG. 1(a) shows the K14-NGF fusion gene contains the mouse NGF cDNA cloned downstream of the human epidermal K14 gene promoter and enhancer sequences (Vassar et al., 1989). A fragment containing a partial sequence of the hGH gene was ligated downstream of the NGF insert to provide an intron containing sequence and poly A (pA) addition signal. Arrow indicates transcription start site. FIG. 1(b) shows a schematic depicting the onset of NGF expression by E11, and its rise and fall at E15. As the endogenous level of NGF decreases, expression of the K14-NGF transgene begins, rises to a steady level and continues in the adult skin. Actual relative levels of expression are not implied. FIG. 1(c) shows mice were screened for the transgene by Southern hybridization of DNA isolated from tail samples obtained three to four weeks after birth. Blots were probed using a $^{32}$P-labeled DNA sequence complementary to the mouse NGF cDNA. The NGF probe detects both the transgene at 1.8 kbp (arrowhead) and the single copy, endogenous NGF gene (1.58 kbp band below the transgene). Three founder animals were isolated: Lane 1, A-39; Lane 2, A-47; Lane 3, A-56; Lane 4, nontransgenic control.

FIG. 2 Expression of the K14-NGF transgene is tissue specific

FIG. 2(a) examines the expression level of the K14-NGF transgene for each line. RNA was isolated from full thickness skin of 4–6 week-old F1 mice and analyzed using Northern hybridization. Ten micrograms of total RNA was resolved on a formaldehyde denaturing gel, transferred to Nytran membrane and probed with a $^{32}$P-labeled DNA sequence complementary to the NGFmRNA. All samples were loaded onto a single gel. Two film exposure were done in order to detect the low level expression of endogenous NGF transcript. Shown is a 3 d exposure, FIG. 2(a) and a 10 d exposure, FIG. 2(b), of the same filter. Lane 1, skin RNA of nontransgenic control. A faint band is visible at 1.3 kb corresponding to the endogenous NGF transcript; lane 2, RNA from tail skin of A-39 founder. Transgene mRNA band (arrowhead) is apparent at the predicted size of 1.9 kb; lane 3, skin RNA of A-47 F1, lane 4, skin RNA of A-56 F1, lane 5, skin RNA of A-47 F1 (loaded twice); lane 6, tongue RNA of A-56 F1. Tongue is a keratinized, K14 keratin expressing structure expected to have transgene expression.

FIG. 2(b) examines the tissue specificity of K14-NGF expression. RNA from brain (lane 7, A-56; lane 13, control), heart (lane 8, A-56; lane 14, control), liver (lane 9, A-56, lane 15, control), and kidney (lane 10, A-56; lane 16, control) were tested. Transgene expression was not evident in these structures, though the 1.3-kb endogenous NGF transcript could be detected in all but liver samples. Lane 11, control skin RNA; lane 12, control tongue RNA. The 28s and 18s ribosomal RNA size markers are indicated by bars on right.

FIG. 3 K14-NGF transgene produces elevated levels of NGF mRNA in skin.

FIG. 3 shows cellular expression of the K14-NGF transgene in skin from A-56 F1 transgenics was examined by in situ hybridization. $^{35}$S-labeled cRNA sense and antisense probes were hybridized to frozen sections of whisker pad skin. Basal cells (arrows) in whisker pad epidermis, FIG. 3(a), and vibrissa, FIG. 3(c), of control animals had silver grain density at background levels. A-56 F1 transgenic mice had a greater labeling density of whisker pad basal cells, FIG. 3(b) (arrows), and vibrissa, FIG. 3(d). Control hybridizations using a sense riproprobe showed background levels of hybridization. Bar=50 μm.

FIG. 4 Expression of K14-NGF causes hyperinnervation of skin.

Overproduction of NGF by the epidermis caused by hyperinnervation that was evident with normal histology. Skin from dorsum, (FIGS. 4a and 4b) and whisker pad (FIG. 4c and 4d) was processed for paraffin histology and sections stained with hematoxylin and eosin. Control skin (FIG. 4a and 4c) had few apparent neuron bundles whereas A-56 F1 transgenic skin (FIG. 4b and 4d) showed numerous, enlarged fiber bundles (arrowheads. * =muscle. Bar=10 μm.

FIG. 5 Immunolabeling of transgenic skin reveals a hyperinnervation of sensory and sympathetic neurons.

Figure 5C:
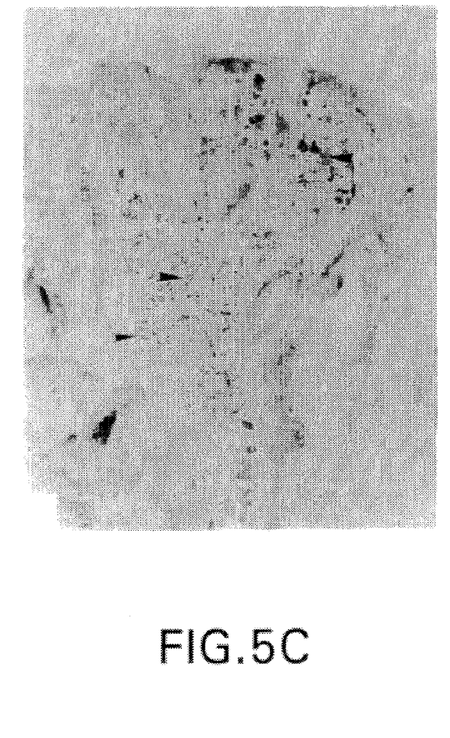
Figure 5D:
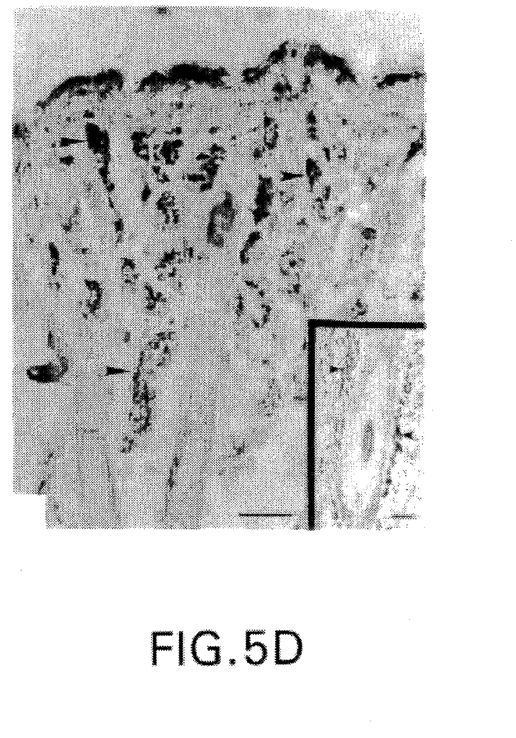

To verify that the fiber bundles in the skin were composed of neuronal processes, frozen sections of whisker pad skin from control (FIG. 5a) and A-56 F1 transgenics (FIG. 5b) were immunolabeled with an antineurofilament 150 antibody followed by incubation with a goat anti-rabbit FITC conjugated secondary. Control skin had immunoreactive fibers (arrowheads) in the reticular layer of the dermis, deep dermis, and around hair follicles and vibrissa (arrow). A significant increase in the number of fibers and bundles was seen in an equivalent region of A-56 transgenic skin (FIG. 5b). To determine whether the large nerve bundles in the A-56 skin contained sympathetic fibers, sections were immunolabeled with an anti-TH antibody followed by a biotinylated goat-anti rabbit secondary processing with DAB (FIG. 5c). TH positive fibers, which were rare in control skin, were found throughout the dermis (arrowheads). To examine peripheral sensory fibers in the transgenic skin, A-56 F1 transgenics were labeled with anti-CGRP followed by a biotinylated goat-anti rabbit secondary antibody (FIG. 5d). Large numbers of CGRP positive fibers and nerve bundles were present in the dermis and around vibrissa. Inset shows vibrissa surrounded by CGRP positive fibers (arrowheads). Bar=5 μm.

FIG. 6 Expression of K14-NGF causes enlargement of the trigeminal and superior cervical ganglia.

Trigeminal ganglia (FIG. 6a) and superior cervical ganglia (FIG. 6b) were removed from control A-48 F1, and A-56 F1 mice. For both the trigeminal and sympathetic superior cervical ganglia, controls (left) were smaller than either the A-48 (center) or A-56 ganglia (right. Bar=1 mm).

The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of the disclosed embodiments. It is to be understood that the phraseology or terminology employed herein is for the purpose of description only and not of limitation. It is obvious that certain changes and modifications may be practiced within the scope of the appended claims.

We claim:

1. A transgenic mouse whose somatic and germ cells contain and express a gene encoding for mouse nerve growth factor, said mouse exhibiting hyperinnervation when compared to a normal mouse, and said gene having been introduced into fertilized mouse embryo of said mouse or an ancestor of said mouse by microinjection, and wherein said gene is introduced into said mouse as plasmid k14-NGF-hGH, deposited as of ATCC Accession.

2. The mouse of claim 1, wherein said mouse is fertile and capable of transmitting said gene to its offspring.

3. The mouse of claim 1, wherein said plasmid k14-NGF-hGH comprises a 1.8 kbp sequence encoding the human growth hormone gene.

4. The mouse of claim 1, wherein said mouse has a phenotype characterized by hyperinnervation of the skin, hypertrophy of the trigeminal ganglion and enlargement of the superior cervical sympathetic and dorsal root ganglia when compared to a normal mouse.

5. A method of producing the mouse of claim 1, which comprises:

(a) providing a mouse nerve growth factor gene plasmid k14-NGF-hGH, deposited as of ATCC Accession No. 69423;

(b) introducing said gene into a fertilized mouse embryo by microinjection;

(c) transplanting said embryo into a pseudopregnant mouse; and (d) allowing said embryo to develop to term.

* * * * *